United States Patent [19]
Calvert

[11] Patent Number: 5,728,053
[45] Date of Patent: Mar. 17, 1998

[54] CATHETER CAST

[76] Inventor: Nathaniel Calvert, 3102 Crescent La. NW., Rochester, Minn. 55901

[21] Appl. No.: 685,891

[22] Filed: Jul. 25, 1996

[51] Int. Cl.⁶ .................................................. A61F 5/00
[52] U.S. Cl. ............................ 602/5; 128/877; 128/878; 128/879
[58] Field of Search ............................ 128/869, 877, 128/878, 879; 602/5, 12, 13, 15, 16, 20, 21, 23, 24

[56] References Cited

U.S. PATENT DOCUMENTS

| | | | |
|---|---|---|---|
| 1,326,717 | 12/1919 | Ellis | 602/5 |
| 1,741,011 | 12/1929 | Carvill | 602/5 |
| 3,176,683 | 4/1965 | Posey | 128/879 |
| 3,580,248 | 5/1971 | Larson | 602/12 |
| 3,976,066 | 8/1976 | McCartney | 128/879 |
| 5,339,834 | 8/1994 | Marelli | 128/878 |
| 5,577,516 | 11/1996 | Schaeffer | 128/877 |

*Primary Examiner*—Michael A. Brown
*Attorney, Agent, or Firm*—D. L. Tschida

[57] ABSTRACT

A rigid support mounted to protect the site of a connection to a catheter or other in-dwelling treatment assembly. In a forearm cast assembly for a dialysis catheter, a hinged frame is retained to the arm with adjustable elastic strap anchors at the elbow and hand. Top and bottom perforated frame sections are held together with hook and loop hinges and closure fasteners. A variety of detachable, cushioned liners mount to the interior frame surfaces to prevent abrasion or dislodgment of the treatment assembly. The frames are constructed to permit limb movement within the cast with minimal impediment to limb movement about the body. Alternative single and double shell frames are also disclosed which include adjustable harness straps and adhesive retainers to accommodate a variety of mounting sites.

18 Claims, 6 Drawing Sheets

CATHETER CAST

BACKGROUND OF THE INVENTION

The present invention relates to medical casts and, in particular, to a perforated assembly which attaches to a person's body to shroud the site of an in-dwelling catheter connection or other in-dwelling treatment assembly during and between treatments.

Varieties of rehabilative casts are available for protecting the arms, legs, and trunk of the human body. Most typically, rigid casts are semi-permanently mounted to the body to completely shroud an injured body part during treatment. The casts are typically constructed of a wrapped fiber material that is permanently cast to a rigid condition with plaster of Paris or various resins. The casts restrain limb movement within the cast and limb movement relative to the body. With the healing of the injured site, the casts are destroyed during removal.

Varieties of splints are also known which are constructed from semi-rigid and rigid materials. The splint is typically secured to the injury site with disposable wrappings. Protective covers may be separately mounted over the splint.

The principal object of the above devices is to cover and protect an injured limb from external forces during prolonged rehabilitation. Provisions are not made at the cast or splint to permit periodic inspection of the injured site nor permit periodic delivery of medicants to the site. Movement of the covered limb is also restricted.

Many medical treatments require placement of an in-dwelling catheter or other treatment assembly to the body for relatively shorter periods. Depending upon the treatment procedure, a critical connection is made to an appropriate body site to administer medicants and/or couple the patient to stationary or portable treatment or monitoring equipment, for example, kidney dialysis equipment. The treatment procedure may require several hours, several days or a few weeks. During the treatment, the patient's activities and movement is restricted to prevent damage to the treatment site or withdrawal of the treatment assembly.

In-dwelling attachments particularly limit patient freedom, unless protected. Casts and splints are not used or recommended during such treatments, in preference to cautionary couseling to restrict patient movement. The restriction of normal patient activities and lifestyle, over time, can become psychologically draining, especially for procedures that require a long duration treatment regime and/or frequent treatments. The frequency of treatments and injury to the treatment site or necessity to re-attach a treatment assembly can also reduce the number of available attachment sites and compound the problems and duration of the treatment.

The present invention was developed to permit a prolonged attachment of an in-dwelling catheter and allow substantially normal freedom of patient movement, during and between treatments. The cast protects the in-dwelling catheter assembly from dislodgment and the attachment site from abrasion. The assembly overcomes the disadvantages of conventional casts and splints and provides perforations in the cast to expose the treatment site and permit necessary, periodic access. The cast is also constructed to permit periodic removal for cleaning and/or changing of appended dressings and cushions.

SUMMARY OF THE INVENTION

It is a primary object of the invention to provide a rigid detachable assembly for physically shrouding a treatment site, yet permitting periodic access to the site without destroying the shroud.

It is a further object of the invention to provide a rigid frame having at least one treatment aperture, which protects, yet exposes, the treatment site and includes a plurality of straps for retaining the frame to the body.

It is a further object of the invention to provide a rigid frame having a treatment aperture, which provides a protected exposure of the treatment site and includes an adhesive fastener system for retaining the frame to the body.

It is a further object of the invention to provide a cast having first and second frame sections, which sections mount to opposite surfaces of a limb and include a number of cushioned apertures through which a treatment assembly is exposed.

It is a further object of the invention to provide a rigid frame which permits limb movement within the cast and supports one or more suitable cushions to prevent skin abrasion or dislodgment of the treatment assembly.

It is a further object of the invention to provide flexible hinge and strap retainers, constructed of hook and loop fastener material, to secure the mating frame sections to a limb and length adjustable straps which mount about the hand and elbow to retain and position the cast to the arm.

It is a still further object of the invention to provide a removeable cloth cover for the cast.

Various of the foregoing objects, advantages and distinctions of the invention are obtained in a number of presently preferred constructions which are described with respect to the appended drawings. In a first construction compatible with an in-dwelling dialysis catheter, a multi-section frame is provided. The frame is secured about the forearm and positioned between the elbow and the hand with a pair of elastic straps. Hook and loop fasteners at the frames permit adjusting the mounting of the frames and also permit periodic removal.

First and second frames particularly mount to opposite sides of the forearm and separately support detachable cushions. A number of apertures are provided through at least one of the frames to expose and provide access to an aligned in-dwelling treatment assembly and vent the space between the cast and arm. Lengths of mating hook and loop fastener material are longitudinally and transversely mounted to the frames to hinge and secure one to the other. A cloth cover includes other mating hook and loop fasteners and mounts over the assembled cast. The frames are sized to permit limb movement within the cast.

In an alternative cast, a single, concave frame includes one or more apertures. The profile of the frame is shaped to cover a treatment site. The frame mounts to a limb with elastic straps containing hook and loop fasteners.

In another construction, a single, perforated frame having a treatment aperture includes adhesive backed hook and loop fastener strips which secure the frame to the skin.

Still other constructions, objects, advantages and distinctions of the invention will become more apparent from the following description with respect to the appended drawings. To the extent modifications and improvements have been considered, they are described as appropriate. The description should not be literally construed in limitation of the invention, which should be interpreted within the scope of the further appended claims.

DESCRIPTION OF THE PREFERRED EMBODIMENT

Figure 1:
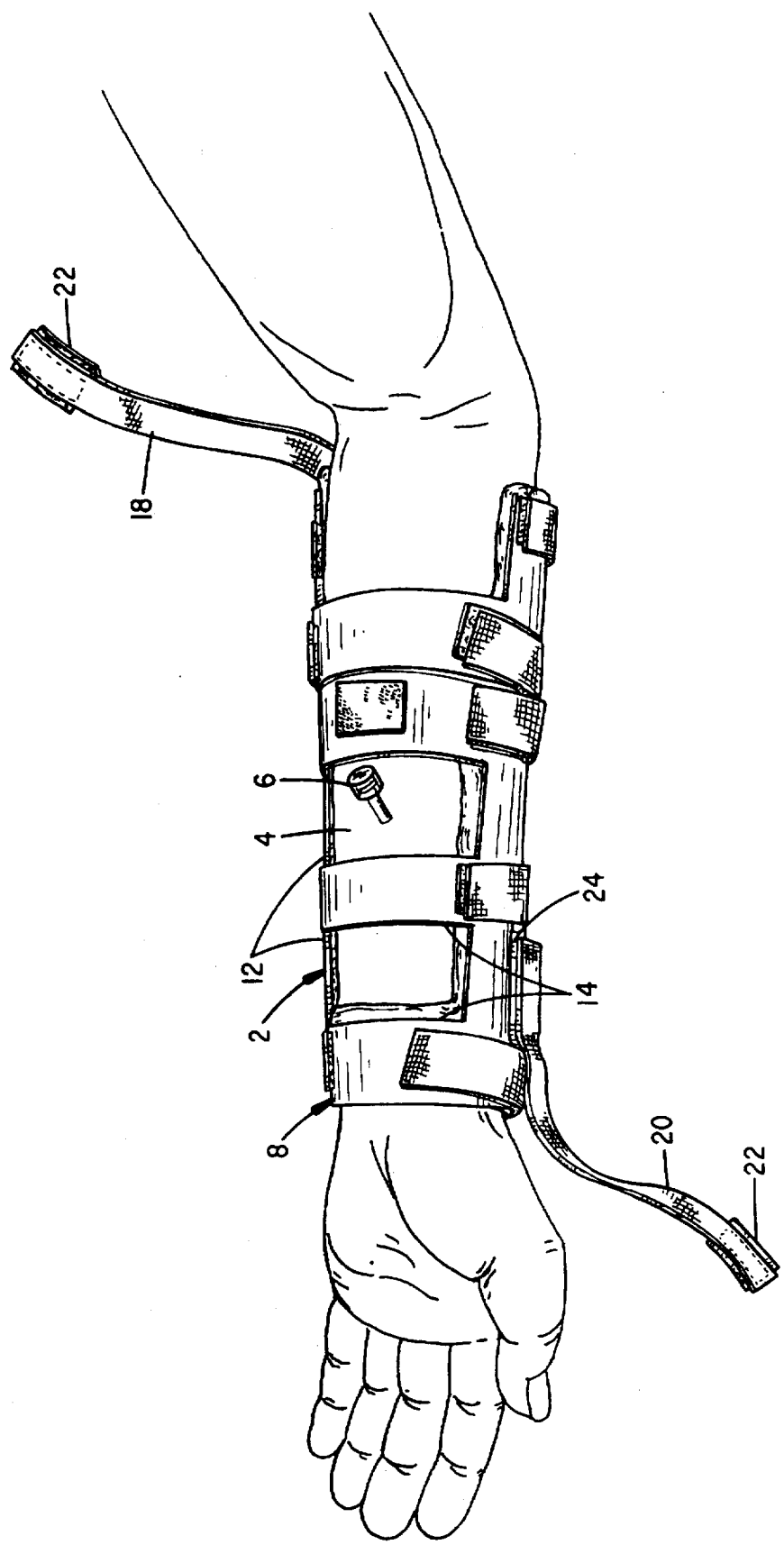
FIG. 1 is a perspective drawing to a dialysis cast mounted to a patient's forearm to protect an access port to an FIG. 2 is an exploded assembly drawing to the frames of the cast of FIG. 1 and the appended hinge, cushioned liners, fasteners and hand and elbow positioners.
Figure 2:
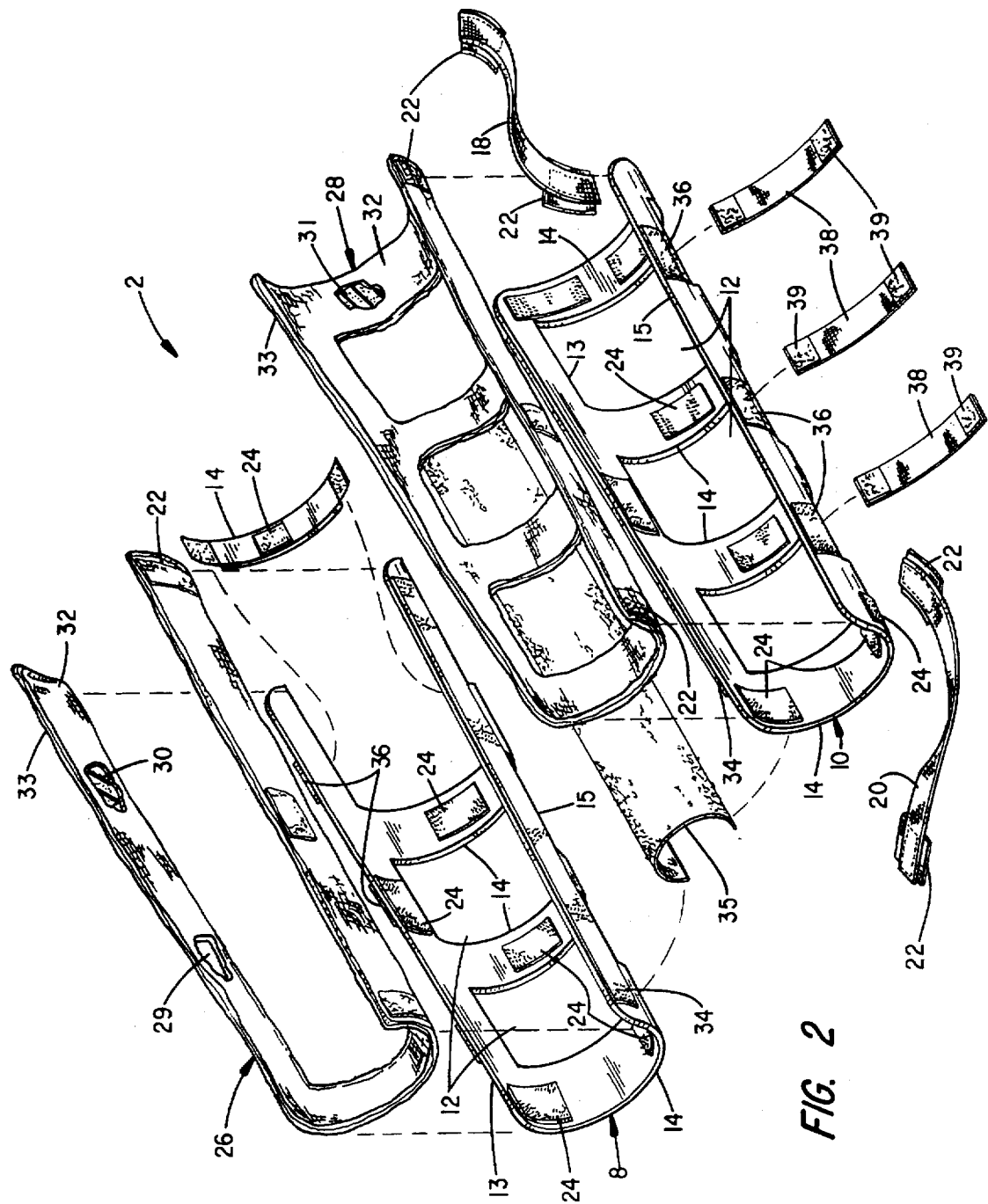
Figure 3:
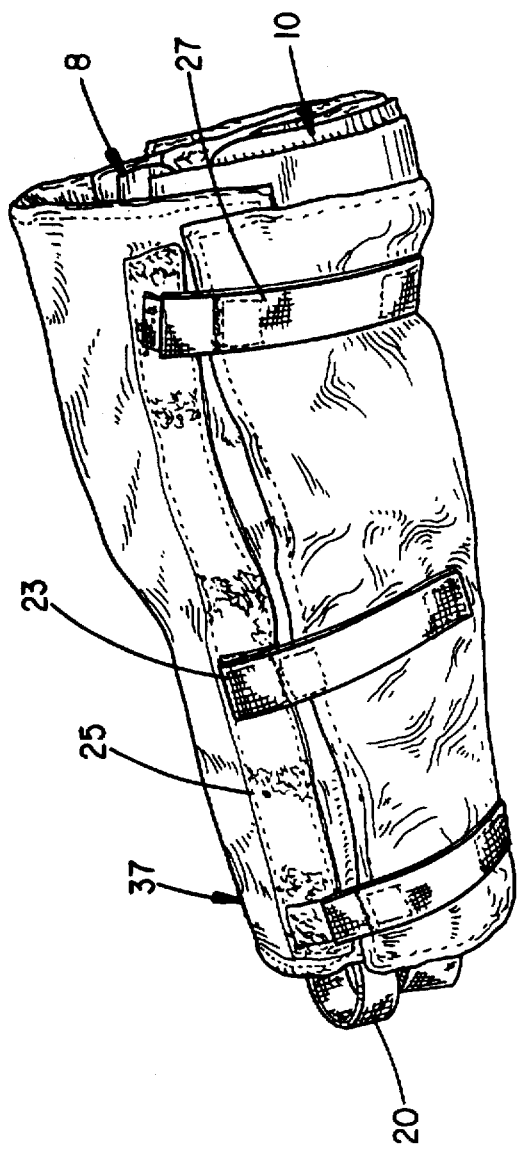
FIG. 3 is a perspective drawing to the assembled cast of FIG. 1 when covered with a protective cloth cover.

Referring to FIGS. 1 through 3, details are shown to a treatment cast 2 which mounts to the forearm to protect a treatment site 4. A treatment assembly 6, such as an in-dwelling access port to a dialysis catheter, is mounted at the site 4. The cast 2 provides a pair of upper and lower concave frames 8 and 10 which are shaped to mount around the forearm and protect the port 6. The frames 8 and 10 are sized to permit the arm to rotate normally within the frames without contacting the port 6.

Each of the frames 8 and 10 includes a number of apertures 12. The apertures 12 are defined between cross braces 14, reference FIG. 2. The apertures 12 are sized and positioned to appropriately shroud or shield the treatment site 4 and prevent dislodgment of the assembly 6, yet expose the assembly 6 to facilitate periodic access during treatments. That is, the assembly 6 is periodically coupled to portable and stationary dialysis equipment.

Although rectangular apertures 12 are depicted, the shape, spacing relative sizes and number of apertures 12 and the elevation of each aperture 12 above the assembly 6 can be varied to accommodate a variety of differing treatment assemblies 6. The shape of the frame sections 8 and 10 may also be tailored or customized to mount to other treatment sites 4, such as at the upper arm, leg or to the trunk of the body. The peripheral edges of each frame 8 and 10 at the apertures 12 may also include raised surfaces (not shown) of any variety of shapes to accommodate a necessary profile of any supported treatment assembly 6 at the treatment site 4. Raised channels may also be formed at the frames to space sections of the frames 8 and 10 away from the lower lying skin and permit the routing of conduits through the channels.

Depending on the mounting location to the cast 2 and with attention to FIG. 2, the frame sections 8 and 10 can be constructed to be identical or to exhibit differing shapes. For example, the frame section 8, which mounts to the inside of the forearm, includes one less cross piece 14 at the aft end of the frame 8 than the frame 10. The frame 8 thereby accommodates bending movements of the arm. Although multiple frame sections 8 and 10 are used at the cast 2, fewer frame sections might be required and examples of which are disclosed below at the discussion to FIGS. 4 and 5. Frames of three or more sections may also be required in certain circumstances.

More or less apertures 12 can also be accommodated with detachable cross braces 14. That is, the cross braces 14 can be constructed to attach to the longitudinal rails 13 and 15 with hook and loop or VELCRO fasteners 17 or other mechanical fasteners.

Presently the frame sections 8 and 10 are formed from separate rigid molded plastic pieces. Preferred plastics should be capable of being sterilized and be approved for medical applications. A variety of other materials or combinations, such as metals, laminates, and fiberglass or other fiber/resin composites of each may be used. Other desired characteristics, are that the material be light weight and durable and be able to withstand periodic cleaning and the forces of normal bumps and the like, without deforming or permitting the dislodgement of the treatment assembly 6.

Necessary support to anchor and stabilize the mounting location of the cast 2 and one of the apertures 12 relative to the treatment site 4 is obtained with an elbow strap 18 and a hand strap 20. The straps 18, 20 are constructed of lengths of elastic webbing. Sewn to the ends of the webbing are tabs 22 of hook and loop fastener material. Mating tabs 24 are bonded to the frame sections 8 and 10. Upon mounting the cast 2 to the forearm, the straps 18 and 20 are trained to stretch. A resilient anchor is thus obtained which maintains the location of the cast 2 at the forearm. That is, the relative length of the straps 18 and 20 are adjusted. Once set, the resilience of the elastic straps 18 and 20 counteract one another to retain the cast 2 at an equilibrium position.

Figure 4:
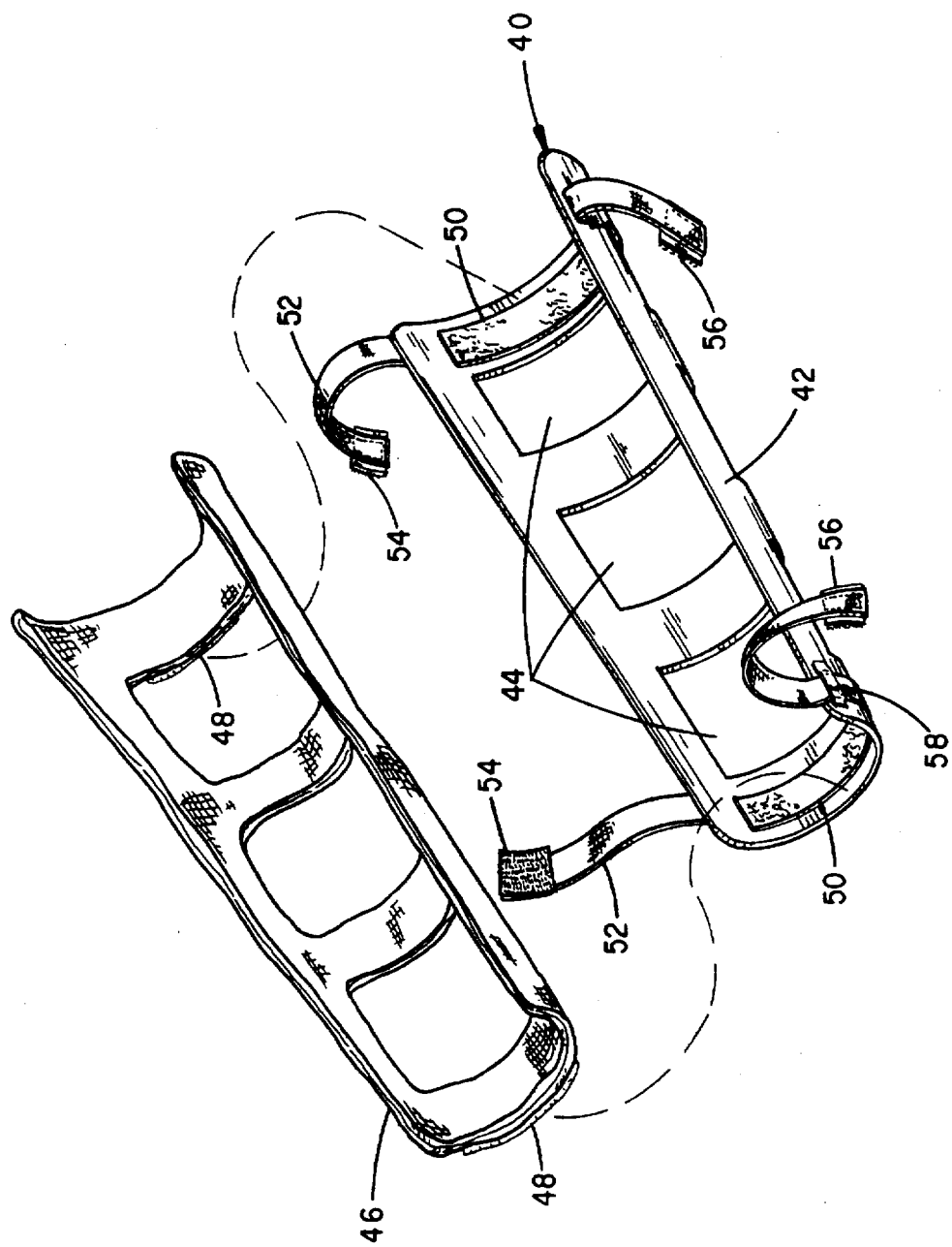
FIG. 4 is a perspective drawing shown in exploded assembly to a single frame cast having a removeable cloth liner and elastic retainer straps.
Figure 5:
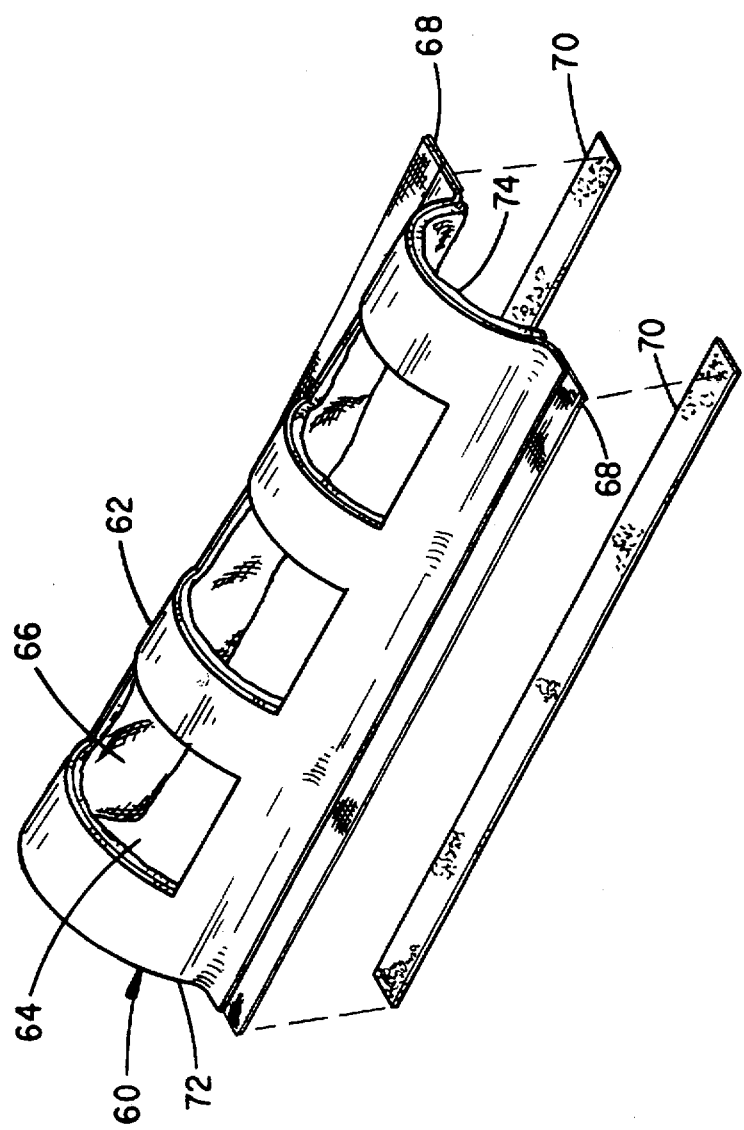
FIG. 5 is a perspective drawing to a single frame cast having a cloth liner and adhesive bound hook and loop fastener strips.

Inelastic straps may be used in lieu of the resilient straps 18 and 20. In some circumstances, only a single strap may be required. The cast 2 might also be retained to the forearm with tape or other fasteners which fix the cast to the arm. Examples of the later mountings are shown at FIGS. 4 and 5.

Mounted to the interior surfaces of the frames 8 and 10 are cushioned liners 26 and 28. The liner 26 exhibits a shape complimentary to the inner frame 8 and the liner 28 exhibits a shape complimentary to the outer frame 10. The liners 26, 28 are retained to the frames 8 and 10 with hook and loop tabs 22 and 24 that are sewn to the liners 32, 33 and bound to the frame sections 8 and 10. The liners 26 and 28 cushion the arm against abrasion from the frame sections 8 and 10 and shocks which are absorbed by the frames 8 and 10.

The liners 26 and 28 each include a soft core 30, 31 which is covered over with sewn, medical grade fabric covers 32, 33. The fabric covers 32 and 33 absorb and wick away any perspiration. The mating tab fasteners 22, 24 at the liners 26 and 28 and the frame sections 8 and 10 permit periodic removal, cleaning, and replacement or sterilization of the liners 26, 28 and/or covers 32, 33. Presently a foam cushioning material is used at the cores 30 and 31.

A variety of other cushioning materials might be used, including a liquid filled envelope having a complementary shape to the frames 8 and 10. An exemplary liquid or gel filled envelope 29 is also shown at the liner 26. The envelope 29 is constructed of a pair of bonded, liquid impermeable layers which capture a liquid or gel core material. Comparable cushions are found at bicycle seats.

The frames 8 and 10 are mounted to one another and the arm at hinge strips 34 which are secured along adjoining peripheral, longitudinal rails 13 and 15 of the frames 8 and 10. A cover strip 35 fastens to both of the strips 34 to complete the hinge.

A series of hook and loop tabs 36 are separately mounted along the longitudinal rails 15, opposite the hinge strips 34 and between the cross pieces 14. Elastic strap retainers 38, which include hook and loop tabs 39, mate to the tabs 36 and extend between the tabs 36 to retain the frames 8 and 10 to one another and to the arm or other body part. Upon removing the hinge strips 35 and/or the strap retainers 38, the cast 2 can be removed from the arm and the frames 8 and 10 can be detached from one another.

Although hook and loop fastener material is presently preferred at the tabs 22, 24, 36 and 39 and the hinge and cover strips 34 and 35, a variety of other mating fasteners can be used to equal advantage to provide an adjustable and detachable mounting of the frames 8 and 10 to the arm and/or the pieces of the frames 8 and 10 to one another. Preferrably, any fastener should permit sterilization.

FIG. 3 depicts the cast 2 covered over with a cloth cover 37 that is wrapped about the frames 8 and 10. The cover 37 finds application in a variety of instances to protect the skin from cold. The cover 37 also permits an overlying shirt of blouse to slide along the cast 2. The cover 37 may be constructed of a water impermeable material to protect the costs 2 and treatment assembly 6 from rain or when bathing.

A strip of hook and loop fastener material 25 is retained to the cover 37 along a longitudinal peripheral edge. A number of straps 27 are sewn at one end to the cover 37. An opposite peripheral edge contains mating hook and loop fastener tabs 23. With the fitting of the cover to the cast 2, the straps 27 are positioned to wrap around the cover 37 such that the tabs 23 mount to the strip 35 and retain the cover 37 to the cast 2.

Turning attention to FIG. 4, a cast 40 is shown that has a single concave frame 42. A number of apertures 44 are provided at the frame 42 which can be aligned to a desired treatment site 4. A cushioned liner 46 is detachably secured to the interior surface of the frame 42 at mating hook and loop tabs 48 and 50 to prevent abrasion and wick away perspiration. The liner 46 consists of cloth covers and between which is fitted a resilient core, such as described above. Straps 52 having mating hook and loop tabs 54 and 56 are threaded through loops 58 at the frame 42 to extend around the frame 42 and the arm and attach one to the other. Alternatively, upon permanently securing one end of the straps 52 to the frame 42, the tabs 56 can be mounted to the frame 42 to mate with the tabs 54. The straps 50 are presently constructed of elastic webbing, although might be constructed of a variety of other rigid or resilient materials.

FIG. 5 depicts yet another cast 60 having a single convex frame 62. The frame 62 includes a number of treatment apertures 64 and a cushion liner 66. The frame 62 can be mounted to a variety of body surfaces, such as at the arm, thigh or abdomen, among other places where strap retainers are not easily accommodated. The cast readily mounts beneath clothing to shroud a medical attachment from abrasion and possible disconnection.

The frame 62 is retained to the body with mating hook and loop strip fasteners 68 and 70. The strips 68 are permanently bound to the peripheral edges of the frame 62. The strips 70, in turn, include a medical grade adhesive on one surface and by which the strips 70 are bound to the body. The opposite surface includes hooks or loops to mate with the strips 68. The cast 60 can thereby be readily mounted to a variety of treatment sites 4 and be removed as necessary to permit mounting a new frame 62 or perform other treatment activities. Once a treatment is completed, the frame 62 is re-attached.

Raised channels 72 and 74 are provided at the ends of the frame 62, for example, to allow the routing of a lower lying catheter or other conduit to pass beneath the frame 62 and along the skin. The cast 60 thus protects not only the connection of tubing to an access port 6 but also a portion of the initial length of catheter tubing, for example, a pubic catheter.

Depending upon the mounting site, the shape and length of the frame 62 can be tailored. For example, the cast 60 might exhibit a hemispherical domed shape or a square or rectangular, domed shape. The numbers of apertures 66 might also be varied. The locations of any apertures 66 and access or egress channels 72, 74 might also be also varied with the forming of the frame 60 or by providing detachable cross braces as discussed above.

Figure 6:
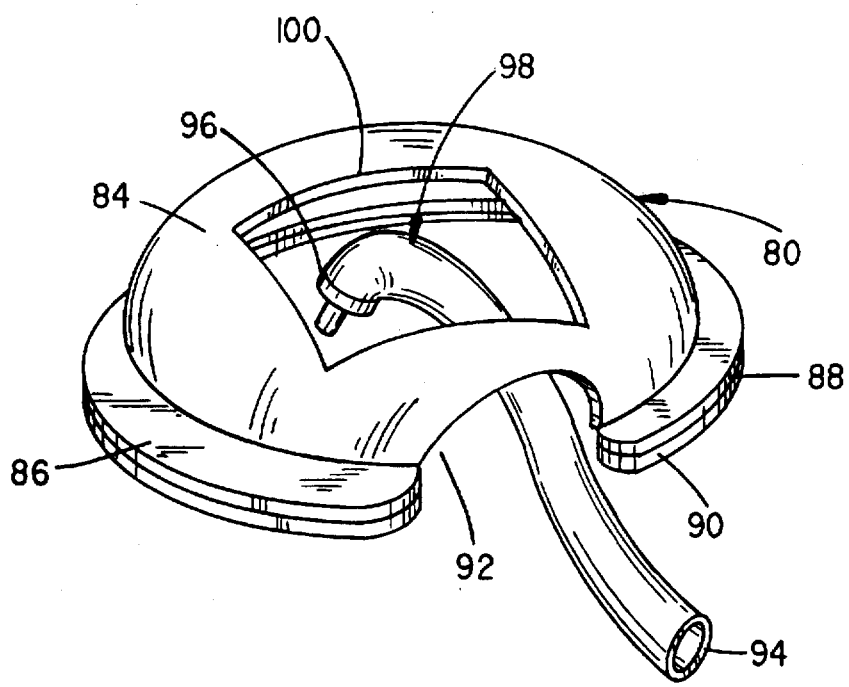
FIG. 6 depicts a patch cast having a hemispherical shape.

FIG. 6 depicts another, domed, adhesive patch cast 80. An aperture 82 is formed in a hemispherical domed, rigid frame 84 which projects above a border 86. A layer 88 of mating hook and loop fastener material is bonded to the border 86. A mating layer 90 mounts to exposed hooks or loops of the layer 28. A medical grade adhesive retains the layer 90 to the skin. A channel 92 shelters a length of tubing 94 which mates to the access port 94 of an in-dwelling treatment assembly 98. The assembly 98 is exposed through an aperture 100.

While the invention has been described with respect to a number of alternative constructions and considered modifications and improvements, still other constructions may be suggested to those skilled in the art. The invention should therefore not be strictly construed in limitation to the foregoing description, but rather should be interpreted to include all those equivalent embodiments within the spirit and scope of the following claims.

What is claimed is:

1. A treatment cast comprising:

a) first and second rigid frames, wherein a plurality of cross braces extend between longitudinal rails of each of said first and second frames, and wherein at least one treatment aperture is defined to expose a treatment site;

b) first and second pliable cushion means for cushioning said first and second frames from abrading contact with the treatment site, wherein said first and second cushion means are nonpermanently secured to said first and second frames with a plurality of sections of mating hook and loop fastener material which fastener sections are mounted to said first and second cushion means and to said first and second frames;

c) hinge means for retaining adjoining longitudinal rails of said first and second frames to one another; and d) retention means for wrapping about said first and second frames to secure the frames to the body, whereby said first and second frames shroud and expose a treatment assembly at a treatment site.

2. Apparatus as set forth in claim 1 wherein said hinge means and said retention means comprise a plurality of interlocking hook and loop fasteners disposed about said first and second frames and arranged to hinge and strap said first and second frames to one another.

3. Apparatus as set forth in claim 1 wherein at least one of said first and second cushion means comprises a fabric cover having a resilient core bound within the fabric cover.

4. Apparatus as set forth in claim 3 wherein said resilient core comprises a liquid impermeable envelope which contains a liquid filler.

5. Apparatus as said forth in claim 1 wherein peripheral edges of at least one of the first and second frames is shaped to define a channel elevated above the body, whereby a portion of the treatment assembly can be routed through said channel and beneath said frame.

6. Apparatus as set forth in claim 1 including strap means which extend from said treatment cast and which is trainable about a portion of the body substantially displaced from the treatment site to juxtaposition the treatment aperture to the treatment site.

7. Apparatus as set forth in claim 1 wherein at least one of said cross braces includes means for nonpermanently securing the cross brace to the longitudinal rails of the one of said first and second frames, whereby the size and location of said treatment aperture can be varied.

8. A treatment cast comprising:
  a) first and second rigid frames, wherein a plurality of cross braces extend between longitudinal rails of each of said first and second frames to define a plurality of apertures, and wherein one of said apertures is shaped to expose a treatment site;
  b) first and second cushions, wherein each of said first and second cushions includes a fabric cover and a resilient core, and wherein a plurality of mating hook and loop fasteners are mounted to said first and second cushions and to said first and second frames to retain said first and second cushions to said first and second frames;
  c) hinge means for retaining adjoining longitudinal rails of said first and second frames to one another; and
  d) retention means for securing said first and second frames to the body, whereby said first and second frames shroud the treatment site and an exposed treatment assembly.

9. Apparatus as set forth in claim 8 wherein said hinge means comprises lengths of mating hook and loop fastener material secured to adjoining longitudinal rails of said first and second frames.

10. Apparatus as said forth in claim 9 wherein said retention means comprises a plurality of resilient straps having tabs of hook and loop fastener material which mate to hook and loop fasteners secured to said first and second frames.

11. Apparatus as said forth in claim 10 including first and second resilient straps which straps are trainable about portions of the body adjoining the treatment site to juxtaposition a treatment aperture to the treatment site.

12. Apparatus as said forth in claim 9 wherein one of said first and second frames includes a raised channel elevated above the body, whereby a portion of the treatment assembly can be routed beneath said frame.

13. Apparatus as said forth in claim 8 including a cover means which wraps about said first and second frames to cover the treatment aperture and including means for securing the cover means to the treatment cast.

14. Apparatus as set forth in claim 8 wherein at least one of said cross braces includes means for nonpermanently securing the cross brace to the longitudinal rails of the one of said first and second frames, whereby the size and location of said treatment aperture can be varied.

15. Apparatus as set forth in claim 8 including strap means which extend from said treatment cast and which is trainable about a portion of the body substantially displaced from the treatment site to juxtaposition the treatment aperture to the treatment site.

16. A treatment cast comprising:
  a) a rigid frame having peripheral edges which contact the body and provide an elevated surface which shrouds a lower lying treatment site, and wherein an aperture at the elevated surface is shaped to expose the treatment site; and
  b) a first strip of a hook and loop fastener material having an adhesive bonded to one surface and which adhesive bonds to the body adjoining the treatment site, and wherein a second strip of hook and loop fastener material is mounted to said frame, whereby upon mounting said first and second strips to one another said frame is secured to the body.

17. Apparatus as said forth in claim 16 wherein said elevated surface exhibits a convex curvature which projects above a circumscribing border and wherein said border includes an elevated channel which extends above the body, whereby a portion of the treatment assembly can be routed through said channel and beneath said frame.

18. Apparatus as set forth in claim 1 wherein said hinge means comprises lengths of mating hook and loop fastener material secured to adjoining longitudinal rails of said first and second frames.

* * * * *